(12) United States Patent
Tian et al.

(10) Patent No.: US 9,320,766 B2
(45) Date of Patent: Apr. 26, 2016

(54) PROTECTIVE EFFECTS AND APPLICATION OF A LACTOBACILLUS PLANTARUM ON THE ALLEVIATION OF LEAD TOXICITY

(75) Inventors: Fengwei Tian, Wuxi (CN); Wei Chen, Wuxi (CN); Qixiao Zhai, Wuxi (CN); Hao Zhang, Wuxi (CN); Jianxin Zhao, Wuxi (CN); Gang Wang, Wuxi (CN); Yuanda Song, Wuxi (CN); Qiuxiang Zhang, Wuxi (CN); Xiaoming Liu, Wuxi (CN); Min Guo, Wuxi (CN); Daming Fan, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 14/118,867

(22) PCT Filed: Jul. 18, 2012

(86) PCT No.: PCT/CN2012/078799
§ 371 (c)(1),
(2), (4) Date: Nov. 20, 2013

(87) PCT Pub. No.: WO2013/127146
PCT Pub. Date: Sep. 6, 2013

(65) Prior Publication Data
US 2014/0369981 A1    Dec. 18, 2014

(30) Foreign Application Priority Data
Feb. 28, 2012   (CN) .......................... 2012 1 0046323

(51) Int. Cl.
*A61K 35/747* (2015.01)
*C12R 1/25* (2006.01)
*A23L 1/30* (2006.01)
*A23C 13/16* (2006.01)
*A23C 19/032* (2006.01)
*A23C 9/123* (2006.01)
*A23C 11/10* (2006.01)
*C12N 1/20* (2006.01)
*A23L 2/38* (2006.01)
*A23L 1/212* (2006.01)

(52) U.S. Cl.
CPC ............. *A61K 35/747* (2013.01); *A23C 9/1234* (2013.01); *A23C 11/106* (2013.01); *A23C 13/16* (2013.01); *A23C 19/032* (2013.01); *A23L 1/212* (2013.01); *A23L 1/3014* (2013.01); *A23L 2/382* (2013.01); *C12N 1/20* (2013.01); *C12R 1/25* (2013.01); *A23V 2002/00* (2013.01); *A23Y 2220/67* (2013.01)

(58) Field of Classification Search
None
See application file for complete search history.

(56) References Cited

PUBLICATIONS

Carvalho et al., Protective effect of sorbitol and monosodium glutamate during storage of freeze-dried lactic acid bacteria, Lait 83 (2003) 203-210.*
Todorov et al., Effect of medium components on bacteriocin production by Lactobacillus plantarum strains ST23LD and ST341LD, isolated from spoiled olive brine, Microbiological Research 161 (2006) 102-108.*
Strasser et al., Influence of lyopholization, fluidized bed drying, addition of protectants, and storage on the viability of lactic acid bacteria, Journal of Applied Microbiology 107, (2009) 167-177.*

* cited by examiner

*Primary Examiner* — Suzanne M Noakes
*Assistant Examiner* — Stephen Chong
(74) *Attorney, Agent, or Firm* — CBM Patent Consulting, LLC

(57) ABSTRACT

The *Lactobacillus plantarum* CCFM8661 is tolerant to acid and lead ions in vitro which can tolerate lead ions solution with the initial concentration of 150 mg/L, and has a strong capability of binding lead ions, which can reduce the lead level in mice blood, liver, kidney and stomach, significantly improve antioxidant indicators and alleviate pathological symptoms of lead exposed mice.

3 Claims, 3 Drawing Sheets

PROTECTIVE EFFECTS AND APPLICATION OF A LACTOBACILLUS PLANTARUM ON THE ALLEVIATION OF LEAD TOXICITY

This application is the U.S. national phase of International Application No. PCT/CN2012/078799 Filed 18 Jul. 2012 which designated the U.S. and claims priority to Chinese Application No. 201210046323.5 filed 28 Feb. 2012, the entire contents of each of which are hereby incorporated by reference.

FIELD OF INVENTION

The present invention relates to the technical field of micro-organisms. More specifically, the present invention relates to the Lactobacillus plantarum that can alleviate lead toxicity, and to the application of said Lactobacillus plantarum.

BACKGROUND OF THE INVENTION

Lead is a heavy metal extremely harmful to human health. With unique physical and chemical properties, lead is widely used in the human society. However, it is also a toxic metal element harmful to a plurality of organs of human, and has no physiological effect in the human body. Therefore, the ideal blood lead concentration should be zero. With rapid development of the industry, agriculture, transportation, paint, printing and electronics industry, lead contaminates the air, soil, water and foods to different extents. The exposure to lead for a long time of gradual contact makes people absorb more lead, resulting in lead accumulation in the body. Lead can directly damage the human health, especially the nervous system, kidneys, hematopoietic system, vascular system and so on. Lead toxicity causes symptoms such as abdominal pain, diarrhea, vomiting, headache, dizziness, coma, and other symptoms, accompanied with vasospasm, liver and kidney damage and other physiological disorders.

Chelating agents such as $EDTANa_2Ca$ and dimercaptosuccinate sodium are most commonly used for the alleviation of lead toxicity. For example, the Chinese Pharmacopoeia, Edition 2 (2000) describes that $EDTANa_2Ca$ is used as an antidote for heavy metal toxicity such as lead and cadmium. However, these drugs have certain side effects. The said calcium EDTA is a chelator with broad spectrum and strong renal toxicity. Moreover, if the drug containing $EDTANa_2Ca$ is administered, a large number of essential trace elements for human body such as zinc, copper, manganese, iron and so on will be excreted with the urine. As these elements are tightly related with the activities of many enzymes, the chelators will endanger human health if used for long time.

For these problems of traditional therapies, it is necessary to find a new intervention or treatment method for lead accumulating and lead toxicity. Lactobacilli are collectively referred to a class of bacteria that can ferment carbohydrates to produce lactic acid. It is widely found in naturally fermented dairy products, fermented plant foods such as pickles, sauerkrauts, silages, and the human intestine. Studies have shown that probiotics including lactobacilli are beneficial bacteria which are essential for the human body and have important physiological functions. The beneficial effects of lactobacilli mainly include: preventing lactose intolerance, tumor and cancer; balancing the human intestinal microflora; promoting the detoxification function of liver and so on. With the exploration of new probiotic functions of lactobacilli, we can put forward some new methods and solutions to alleviate lead toxicity through dietary strategies.

Therefore, it is necessary to screen lactobacilli with the ability of alleviating lead toxicity, and prove that they can play a good role in alleviating lead toxicity in animal models. The applications of these lactobacilli should be developed as well.

DETAILED DESCRIPTION OF THE INVENTION

Technical Question to be Solved

One object of the present invention is to provide a Lactobacillus plantarum CCFM8661.

Another object of the present invention is to provide the application of the said Lactobacillus plantarum CCFM8661.

Technical Plan

The invention is achieved through the following technical solutions.

The present invention relates to an isolated Lactobacillus plantarum CCFM8661, deposited at the General Microbiology Culture Collection Center of China Committee for Culture Collection of Microorganisms under accession number CGMCC No. 5494.

The said Lactobacillus plantarum CCFM8661, which is able (1) to grow well in the environment of pH3.0-9.0 and survive well in the environment of pH2.5;

(2) to be tolerant to lead ions when cultured in lead containing medium in vitro;

(3) to have capability of binding lead ions when incubated in lead containing solution in vitro;

(4) to reduce the lead level in a mammal exposed to lead, and to alleviate the lead toxicity in a mammal exposed to lead.

The present invention also relates to a pharmaceutical composition comprising the said Lactobacillus plantarum CCFM8661 and a pharmaceutically acceptable carrier.

According to an embodiment of the present invention, wherein the said pharmaceutically acceptable carrier is one or more kind(s) of carrier(s) which is or are selected from filler, binder, wetting agent, disintegrant, lubricant or flavoring agent.

According to another embodiment of the present invention, the said pharmaceutical composition is manufactured as granules, capsules, tablets, pills or oral liquid.

The present invention also relates to a fermented food for alleviating lead toxicity comprising the said Lactobacillus plantarum CCFM8661 and an edible composition.

According to another embodiment of the present invention, wherein the said edible composition is selected from the group consisting of a dairy product, a soy product, a fruit and vegetable product.

According to another embodiment of the present invention, wherein the dairy product is selected from the group consisting of milk, sour cream and cheese; the soybean product is selected from the group consisting of soybean milk, fermented soybean and soybean paste; and the fruit and vegetable product is selected from the group consisting of cucumber, carrot, beet, celery and cabbage.

The present invention also relates to the method for preparing the said fermented food, which is comprising: a) providing a fermentation medium that is prepared by mixing water, milk, glucose, tryptone and yeast extract, adjusting pH to neutral, and sterilizing; b) providing a protective agent by mixing skim milk powder, glycerol, malt dextrin, trehalose, L-sodium glutamate and water; c) inoculating said fermentation medium with Lactobacillus plantarum CCFM8661 of claim 1, culturing at 37° C. for 12-24 h, washing 2-4 times with phosphate buffer and re-suspending with said protective agent which yields the medium with the concentration of the *Lactobacillus plantarum* CCFM8661 at the range from $10^9$ to $10^{10}$ CFU/ml; d) culturing at 37° C., and then freeze-drying which yields a starter culture; e) mixing the starter culture with an edible composition at the concentration of the *Lactobacillus plantarum* CCFM8661 above $10^6$ CFU/ml.

The invention also relates to the fermented food prepared according to the method of the invention, wherein the edible composition is selected from the group consisting of a dairy product, a soy product, a fruit and vegetable product.

The invention also relates to the fermented food prepared according to the method of the invention, wherein the dairy product is selected from the group consisting of milk, sour cream and cheese; the soybean product is selected from the group consisting of soybean milk, fermented soybean and soybean paste; and the fruit and vegetable product is selected from the group consisting of cucumber, carrot, beet, celery and cabbage.

The present invention in more details will be described.

This invention relates to a *Lactobacillus plantarum* CCFM8661 which was deposited in the General Microbiology Culture Collection Center of China Committee for Culture Collection of Microorganisms under accession number CGMCC No. 5494.

In accordance with the following criteria, this inventor screens out *Lactobacillus plantarum* CCFM8661 from traditional foods such as pickle and fermented milk wine through a large number of screening experiments, analysis and verification, which is able:

(1) to grow well in the environment of pH3.0-9.0 and survive well in the environment of pH2.5;

(2) to be tolerant to lead ions when cultured in lead containing medium in vitro;

(3) to have capability of binding lead ions when incubated in lead containing solution in vitro;

(4) to reduce the lead level in a mammal exposed to lead, and to alleviate the lead toxicity in a mammal exposed to lead.

The results of these experiments and the analysis and certification are described in detail as follows:

1. It can grow well in the environment of pH3.0-9.0 and survive well in the environment of pH2.5.

Cryo-preserved *Lactobacillus plantarum* CCFM8661 of this invention is inoculated in MRS medium (e.g., Haibo Biotech (Qingdao) Co., Ltd), cultured at 37° C. for 24 h, and then cultured in MRS medium for 2-3 generations. *Lactobacillus plantarum* CCFM8661 culture of 1 mL is taken, inoculated in 19 mL MRS liquid mediums of different pH values (3.0-9.0) respectively, and cultured at 37° C. for 24 h. The initial and final $OD_{600}$ values are measured to determine the cell concentration in the bacterial medium to estimate the growth of bacteria. The $OD_{600}$ value is measured by the absorbance value of the bacterial culture at the wavelength of 600 nm with spectrophotometry. It is usually used to express the cell concentration in bacterial culture media to identify the growth of bacteria in the liquid culture. These test results prove that *Lactobacillus plantarum* CCFM8661 can grow well in the environment of pH 3.0-9.0 so as to carry out the follow-up experiments.

The *Lactobacillus plantarum* CCFM8661 culture is obtained with the culture method mentioned above. The bacteria are washed twice with pH 7.2 PBS (phosphate buffer) of 1.0 mL, and then re-suspended with pH7.2 phosphate buffer of 1.0 mL. The suspension is mixed with pH 2.5 artificial gastric juice of 9.0 mL, and then cultured at 37° C. The samples at the beginning (0 h) and 3 h are respectively taken and cultured in MRS agar medium to count the viable cells and calculate the survival rate. The survival rate refers to the ratio of the logarithm value of viable cell number at 3 h to the logarithm value of viable cell number at 0 h, expressed in %. The strains with the survival rate over 80% are used for the subsequent study of this invention.

The results show that the survival rate of *Lactobacillus plantarum* CCFM8661 is higher than 90% in the artificial gastric juice of pH2.5, indicating that *Lactobacillus plantarum* CCFM8661 has acid tolerance, and survives well in the environment of pH2.5.

2. It has good tolerance to lead ions when cultured in lead containing medium in vitro;

The tolerance of lactobacilli to lead ions in vitro can be reflected through the growth curve in the media of different lead concentrations. Lead chloride of 0.20 g is added to 1 L of water under aseptic conditions to obtain the lead solution of 150 mg/L. The dry powder of MRS solid medium is dissolved in the lead solution to obtain the MRS medium of 150 mg/L lead ions. Likewise, MRS media of 50 mg/L and 500 mg/L lead ions are prepared respectively. The *Lactobacillus plantarum* CCFM8661 at stable phase is inoculated in the MRS mediums of different lead concentrations by 2% (w/w). The plate count is carried out at 0 h, 2 h, 4 h, 6 h, 8 h, 12 h, 16 h, 20 h, and 24 h to obtain the growth curve of *Lactobacillus plantarum* CCFM8661, which is shown in FIG. 1.

FIG. 1 shows that the *Lactobacillus plantarum* CCFM8661 of this invention has good tolerance to lead ions.

3. It can bind lead ions well when incubated in the lead solution in vitro;

Under sterile conditions, seven lactobacilli strains are screened out from traditional fermented foods such as pickle and fermented milk wine according to the acid tolerance screening criteria (strains can grow under pH3.0). One *E. coli* and one *Bacillus subtilis* as control strains and the seven lactobacilli are purified and activated. The mentioned strains are transferred to lead solution of 150 mg/L to make the bacterial concentration at 1 g/L and cultured at 37° C. for 1 h, centrifuged at 6000 rpm for 20 min with Beckman centrifuge, and then washed once with sterile water and centrifuged again. The supernatant is removed and pure nitric acid is added to the bacterial strains, and digested in a microwave digestion oven for 20 min to obtain the digestion solution. The lead ion level in the solution is determined with an atomic absorption spectrometer (Spectr AA 220, Varian, USA) according to the method of Yeager et al. (Yeager D W, Cholak J., Henderson E W, Determination of lead in biological and related materials by atomic absorption spectrometry, Environmental Science and Technology, 1971; 5: 1020-1022.) to determine the capacity of the strains to bind the lead ions. These results are shown in FIG. 2.

FIG. 2 clearly shows that the *Lactobacillus plantarum* CCFM8661 of this invention has better capability of adsorbing lead ions, compared with other test strains and the control strain. Therefore, the *Lactobacillus plantarum* CCFM8661 can bind lead ions well.

4. The effect of alleviating lead toxicity in lead-exposed mice 40 healthy male Kunming mice of 20-25 g are randomly divided into four groups: namely negative control group, lead acetate model group, *Lactobacillus plantarum* CCFM8661 treatment group, and calcium disodium edetate treatment group as positive control. The mice of negative control group are fed with ordinary drinking water and the mice of remaining three groups are fed with 1 g/L lead acetate solution to obtain the lead exposure models. The mice of *Lactobacillus plantarum* CCFM8661 treatment group are daily fed with the $2.0 \times 10^9$ cfu/mL skim milk suspension prepared in Example 3 of Specifications, and the mice of positive control treatment group are intraperitoneally injected with 5 g/L disodium edetate calcium agent every day. The blood of mice is collected at the end of the experiment, and the liver, stomach and kidney are collected after these mice are sacrificed. These organs are processed in accordance with above digestion processes, and then the lead levels can be determined with above atomic absorption spectrophotometry as described by Yeager et al. These results are shown in FIG. 3.

Compared with the lead levels of blood, liver, kidney and stomach as well as anti-oxidation indicators (SOD, MDA) in the lead exposure model group, we find that the *Lactobacillus plantarum* CCFM8661 of this invention can reduce the lead levels in mice blood, liver, kidney and stomach, and significantly improve the anti-oxidation indicators of these mice.

Lead in environment usually enters the human body through digestive tract and respiratory tract, causing acute or chronic toxic effects on digestive, nervous, respiratory and immune systems. It often leads to colic, anemia, muscle and paralysis, and encephalopathy in serious conditions, and even death. Therefore, whether the body is lead poisoned is usually determined according to the *Diagnostic Criteria of Occupational Chronic Lead Toxicity* (GBZ37-2002).

In this invention, the term "alleviating lead toxicity" should be understood as the process that the lead toxicity symptoms of the body decrease or disappear. According to the "Technical Specifications of Inspection and Evaluation of Healthcare Foods" issued by Ministry of Health of China in 2003, the research shows that the pharmaceutical compositions containing *Lactobacillus plantarum* CCFM8661 of this invention can reduce the lead levels of blood, liver and kidney tissue, relieve oxidative stress response, alleviate the pathological symptoms, increase the glutathione level and decrease the malondialdehyde level of these poisoned mice. Thus it has the healthy function of decreasing lead levels in vivo.

The said *Lactobacillus plantarum* CCFM8661 of this invention has the following characteristics:

(1) With acid tolerance, it can grow well in the environment of pH3.0-9.0 and survive well in the environment of pH2.5;

(2) It has good tolerance to lead ions when cultured in lead containing medium in vitro;

(3) It has good capability of adsorbing lead ions when incubated in lead solution in vitro;

(4) It can reduce the lead level of the mice exposed to lead and alleviate the lead toxicity in the mice exposed to lead.

Bacterial characteristics: Gram staining positive, rod-shaped cells of about 0.5-1.0 μm in width and 2-4 μm in length, single, pair or chain, no spores, and two round ends.

Colony characteristics: distinct colonies on the MRS medium with the diameter of 0.3-2.0 mm, round, neat edges, white and opaque appearance, smooth and wet surface, and no pigment.

Growth characteristics: This strain can grow at the optimum temperature of 30-37° C. (the lowest temperature of 20° C., and the highest temperature of 40° C.), in the optimum initial pH of 6.0 (the minimal initial value of pH 2.5 and the maximal initial value of pH 9.0). The *Lactobacillus plantarum* CCFM8661 of this invention has a relatively short lag phase, enters the logarithmic phase at 4 h around, and reach the stable phase at 12 h.

The preservation method for the *Lactobacillus plantarum* CCFM8661 of this invention is as follows:

The original strain of the *Lactobacillus plantarum* CCFM8661 of this invention should be stored at −75° C. in glycerol suspension by 30% (w/w), or stored as dried powder at 4° C.

The culture methods and conditions of the *Lactobacillus plantarum* CCFM8661 of this invention is as follows: it should be cultured in the MRS medium at 37° C. for 18-36 h before use.

This invention also relates to the preparation of pharmaceutical compositions and fermented foods for relieving lead toxicity with the said *Lactobacillus plantarum* CCFM8661.

The said pharmaceutical compositions consist of the *Lactobacillus plantarum* CCFM8661 agent and pharmaceutically acceptable carriers.

According to this invention, the said bacterial agent is usually made of the dry powder prepared with the bacterial solution containing the said *Lactobacillus plantarum* CCFM8661 by the freeze-drying technique or other methods such as spray drying method.

The said *Lactobacillus plantarum* CCFM8661 agent contains viable *Lactobacillus plantarum* CCFM8661 of over $10^6$ CFU/mL.

The determination method of said *Lactobacillus plantarum* CCFM8661 is the MRS plate count method, which is well known to those skilled in the art.

For the said pharmaceutical composition, the said *Lactobacillus plantarum* CCFM8661 accounts for 15-35% weight of pharmaceutical compositions, preferably 18-32%, and more preferably 20-30%.

According to the present invention, the pharmaceutically acceptable carrier refers to the conventional pharmaceutical carrier in the pharmaceutical field, for example, one or more carrier(s) selected from pharmaceutically common fillers, binders, wetting agents, disintegrants, lubricants and flavoring agents.

According to this invention, the filler should be understood as the auxiliary diluent that can increase the weight and volume of the tablet to facilitate tabletting, or the auxiliary absorbent that can absorb excess liquid of the raw materials.

The said filler is selected from starch, sucrose, lactose, calcium sulfate or microcrystalline cellulose.

Preferably, the said filler is selected from starch, sucrose or microcrystalline cellulose.

More preferably, the said filler is selected from starch or microcrystalline cellulose.

According to this invention, the wetting agent should be the liquid that has no stickiness itself, but can wet and stick pharmaceutical raw and auxiliary materials together to obtain granules.

The said wetting agent is selected from water, ethanol, starch or syrup.

Preferably, the said wetting agent is selected from water, ethanol, or starch.

The amount of wetting agent in this invention should be 0.1-3.0% of the total weight of the pharmaceutical compositions.

According to this invention, the said binder should be a sticky material that can be added for granulation if the drug itself has no stickiness or poor stickiness. The sticky material is called as binder.

The said binder is selected from cellulose derivatives, alginate, gelatin, or polyvinyl pyrrolidone.

Preferably, the said binder is selected from cellulose derivatives, gelatin, or polyvinyl pyrrolidone.

More preferably, the said binder is selected from gelatin or polyvinyl pyrrolidone.

The amount of binder in this invention should be 0.5-5.0% of the total weight of the pharmaceutical composition.

According to this invention, the disintegrant should be understood as an auxiliary material that can facilitate the pharmaceutical composition to rapidly disintegrate into small particles in gastrointestinal fluid if added into tablets. It is known that the tablets are very hard after compression. The tablets without the auxiliary material of promoting disintegration are disintegrated slowly in the gastrointestinal tract, which affects the efficacy of the pharmaceutical composition.

The said disintegrant is selected from sodium carboxymethyl starch, hydroxypropyl cellulose, cross-linked carboxymethyl cellulose, agar, calcium carbonate or sodium bicarbonate.

Preferably, the said disintegrant is selected from sodium carboxymethyl starch, hydroxypropyl cellulose, cross-linked carboxymethyl cellulose, agar or sodium bicarbonate.

More preferably, the said disintegrant is selected from sodium carboxymethyl starch, hydroxypropyl cellulose, cross-linked carboxymethyl cellulose, or sodium bicarbonate.

The amount of disintegrant in this invention should be 5.0-15.0% of the total weight of the pharmaceutical composition.

According to this invention, the lubricant should be a chemical that can facilitate the tablet material to flow in the granulation process, prevent the tablet material from sticking to the tableting machine, and help the tablets be released from the mold.

The said lubricant is selected from talcum powder, calcium stearate, magnesium stearate, aerosil, or polyethylene glycol.

Preferably, the said lubricant is selected from talcum powder, calcium stearate, magnesium stearate or polyethylene glycol.

More preferably, the said lubricant is selected from talcum powder or calcium stearate.

The amount of the lubricant in this invention should be 0.5-3.0% of the total weight of the pharmaceutical composition.

According to this invention, the said flavoring agent refers to a pharmaceutical excipient that can reduce or remove the unfavorable taste and odor of the drug so that patients are hard to feel strong bitter or other odors, such as spicy and pungent odors.

For example, the flavoring agent can be selected from the sweeteners such as simple syrup, sucrose, lecithin, orange syrup or cherry syrup; the aromatics such as lemon oil, fennel oil, or peppermint; the mucilages such as sodium alginate, arabic gum, gelatin, methyl cellulose or sodium carboxymethyl cellulose; and the effervescent mixed with citric acid, tartaric acid and sodium bicarbonate.

Preferably, the flavoring agent is selected from the sweeteners such as simple syrup, sucrose, orange syrup or cherry syrup; the aromatics such as lemon oil or peppermint; the mucilages such as sodium alginate, arabic gum, gelatin or sodium carboxymethyl cellulose; and the effervescent mixed with tartaric acid and sodium bicarbonate.

More preferably, the flavoring agent is selected from the sweeteners such as sucrose, orange syrup or cherry syrup; the aromatics such as lemon oil; the mucilages such as sodium alginate or arabic gum; and the effervescent mixed with tartaric acid and sodium bicarbonate.

The amount of the flavoring agent in this invention should be 0.5%-2.0% of the total weight of the pharmaceutical composition.

Lactobacillus plantarum CCFM8661 of this invention with pharmaceutically acceptable carriers or excipients can be made into various dosage forms, such as granules, capsules, tablets, pills or oral liquid, wherein the pharmaceutically acceptable carriers or excipients may be selected depending on the dosage form. These carriers or excipients and their dosages are easy to identify and well known for common technicians in the pharmaceutical field.

In the present invention, the conventional methods and devices known to those skilled in the pharmaceutical field are applied in the preparation of the granules, capsules, tablets, pills or oral liquid.

In general, the "dosage form" should be the single dosage form applicable to the human body, which contains the expectable amount of active substances, for example, the Lactobacillus plantarum CCFM8661 agent of this invention.

In this invention, the said fermented foods are fermented dairy product, soy product, and fruit and vegetable product produced with the starter culture containing the Lactobacillus plantarum CCFM8661 agent.

The said starter culture is prepared by the following steps:

A. Preparation of the medium: water of 87.7% total weight of the medium is used to dissolve 10% of enzymatic hydrolysed skim milk, 0.5% of glucose, 1.5% of tryptone, 0.3% of yeast extract, and then the pH value is adjusted to 6.8, thus obtaining the said medium;

B. Preparation of the protective agent: the protective agent is mixed with water to make the said protective agent containing 100 g/L defatted milk powder, 30 mL/L glycerol, 100 g/L malt dextrin, 150 g/L trehalose, and 10 g/L L-sodium glutamate;

C. The Lactobacillus plantarum CCFM8661 by 2-4% weight of the said medium are inoculated in the medium which has been sterilized at 110-120° C. for 8-12 min, and cultured at 37° C. for 18 h, washed 2-4 times with pH7.2 phosphate buffer and re-suspended with the said protective agent to obtain a medium of $10^{10}$ CFU/ml. The suspension is cultured at 37° C. for 60 min, and then freeze-dried to obtain the said starter culture.

The said dairy product can be milk, sour cream or cheese.

In this invention, the said milk should be cow milk, horse milk or reconstituted milk. The reconstituted milk is prepared with milk powder of 10-15% total weight and demineralized water of 85-90% total weight. The milk powder is now widely commercially available at the market.

The sour cream is prepared with watery cream fermented by lactobacilli. The sour cream offers several advantages over cream topping such as with stronger fragrance and higher production. In addition, lactobacilli can inhibit harmful microorganisms, so the product has lower risk of microbial contamination after disinfection.

The cheese is the food made from fermented cow milk with high nutritional value.

The soy product can be soy milk, fermented soya beans or soybean paste. They are all Chinese traditional foods or flavourings.

The fruit and vegetable products are cucumber, carrot, beet, celery or cabbage products.

In production of dairy, soy, fruit and vegetable products, the starter culture of Lactobacillus plantarum CCFM8661 agent is used according to the following methods:

Generally, the starter culture of Lactobacillus plantarum CCFM8661 agent of this invention is inoculated in raw materials to be treated in conventional production process of dairy, soy, fruit and vegetable products. The product is fermented at the appropriate temperature and pressure for Lactobacillus plantarum CCFM8661 to grow and reproduce. Therefore the product has some acidity, fragrant flavors and other excellent characteristics due to the bacterial metabolites, which also extend the shelf life and improve the nutritional value and digestibility of the product.

[Beneficial Effects]

The Lactobacillus plantarum CCFM8661 of this invention has good tolerance to acid and lead ions in vitro. It can tolerate lead ions solution with the initial concentration of 150 mg/L, and has strong binding capability of lead ions, which can reduce lead levels in mice blood, liver, kidney and stomach, significantly improve the antioxidant indicators and alleviate the pathological symptoms of lead poisoning mice. *Lactobacillus plantarum* CCFM8661 has extensive application prospects in producing pharmaceutical compositions and fermented foods of alleviating lead toxicity.

Wherein: CCFM8661, 14 and ST-3 are *Lactobacillus plantarum*; 2-2 is *Lactobacillus gasseri*; 2-3 is *Lactobacillus rhamnosus* LGG; 22 is *Bifidobacterium bifidum*; and 23 is *Lactobacillus delbrueckii*. *Bacillus subtilis* (*B. subtilis*) and *Escherichia coli* (*E. coli*) are used as control strains in this experiment.

Figure 3:
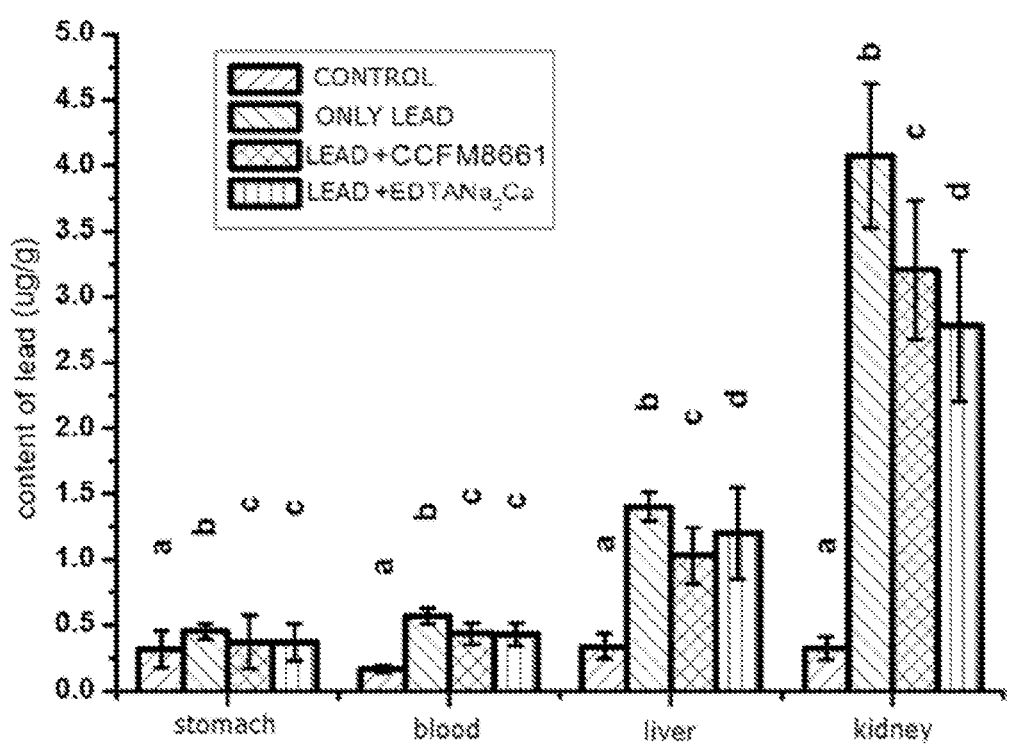

FIG. 3 shows the effect of *Lactobacillus plantarum* CCFM8661 reducing the lead levels in blood, liver, kidney and stomach of the lead-exposed mice;

Groups with different letters (a, b, c, d) differ significantly ($P<0.05$).

SPECIFIC EMBODIMENTS

Example 1

Experiment of Determining the Tolerance of *Lactobacillus plantarum* CCFM8661 to Lead Ions Lead chloride of 0.20 g is added to 1 L of sterile water under aseptic conditions to obtain the aqueous solution of 150 mg/L lead ions. The components of MRS medium are dissolved in the solution to obtain the MRS medium containing 150 mg/L lead ions. Common MRS medium contains tryptone, yeast extract, glucose, sodium acetate, diammonium citrate, Tween-80, magnesium sulfate, manganese sulfate with the pH value of 6.2-6.4.

Figure 1:
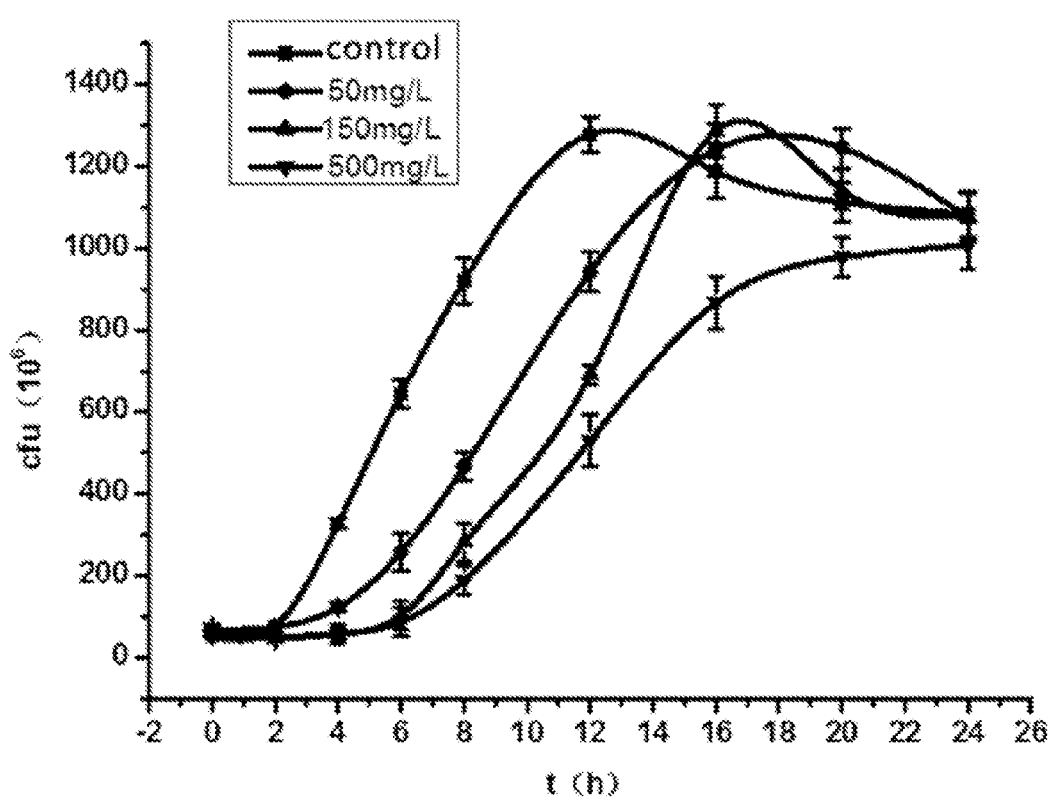
FIG. 1 shows the growth curve of *Lactobacillus plantarum* CCFM8661 in the medium with initial lead ions concentration of 50 mg/L, 150 mg/L and 500 mg/L.

In the same manner as the previously described, MRS mediums containing 50 mg/L and 500 mg/L lead ions are prepared respectively. Cultures of *Lactobacillus plantarum* CCFM8661 at stable phase is inoculated 1:50(v/v) into MRS medium containing lead ions and were cultured at 37° C. Plate colonies was counted was after 0 h, 2 h, 4 h, 6 h, 8 h, 12 h, 16 h, 20 h, and 24 h of culture to obtain the growth curve of *Lactobacillus plantarum* CCFM8661 as shown in FIG. 1. In addition, 1 mL of bacterial cultures are inoculated in MRS medium without lead ions, which serves as control group, and colony counting is carried out under the same conditions.

FIG. 1 shows that in the medium of 150 mg/L lead ions, the growth of *Lactobacillus plantarum* CCFM8661 is suppressed at the beginning; however, it subsequently grows rapidly, and grows even faster than the control group at 24 h. This suggests that the *Lactobacillus plantarum* CCFM8661 has a good tolerance to lead ions.

Example 2

Lead Binding Experiment of *Lactobacillus plantarum* CCFM8661

Seven lactobacilli strains are screened out from Chinese traditional foods such as pickle and fermented milk wine according to the acid tolerance screening criteria (strains can grow under the pH3.0 condition). The seven lactobacilli strains, together with one *E. coli* stain and one *Bacillus subtilis* as control strains are purified and activated using MRS medium for lactobacilli, and LB medium for *E. coli* and *Bacillus subtilis*. The said LB medium is well known to the technicians in the microbial field, which contains tryptone, yeast extract, NaCl, and agar with the pH value of 7.0. These activated bacterial solutions are vibrated uniformly and centrifuged at the speed of 6000 r/min for 15 min. The bacterial pellets of these strains are transferred to the container containing 150 mg/L lead ion solution, while the bacterial pellets of control group are transferred into deionized water to give a final cell concentration of 1 g/L. The samples containing the strains are cultured at 37° C. for 1 h, centrifuged with Beckman centrifuge at the speed of 6000 r/min for 20 min, then washed with sterile water and centrifuged again. The bacterial pellets are added with pure nitric acid after the supernatant is removed, cells, and digested in a microwave digestion oven for 20 min to obtain the digestion solution. The lead ion level in the solution is detected with an atomic absorption spectrometer (Spectr AA 220, Varian, USA) according to the method of Yeager et al to judge the capacity of the strains adsorbing lead ions.

Figure 2:
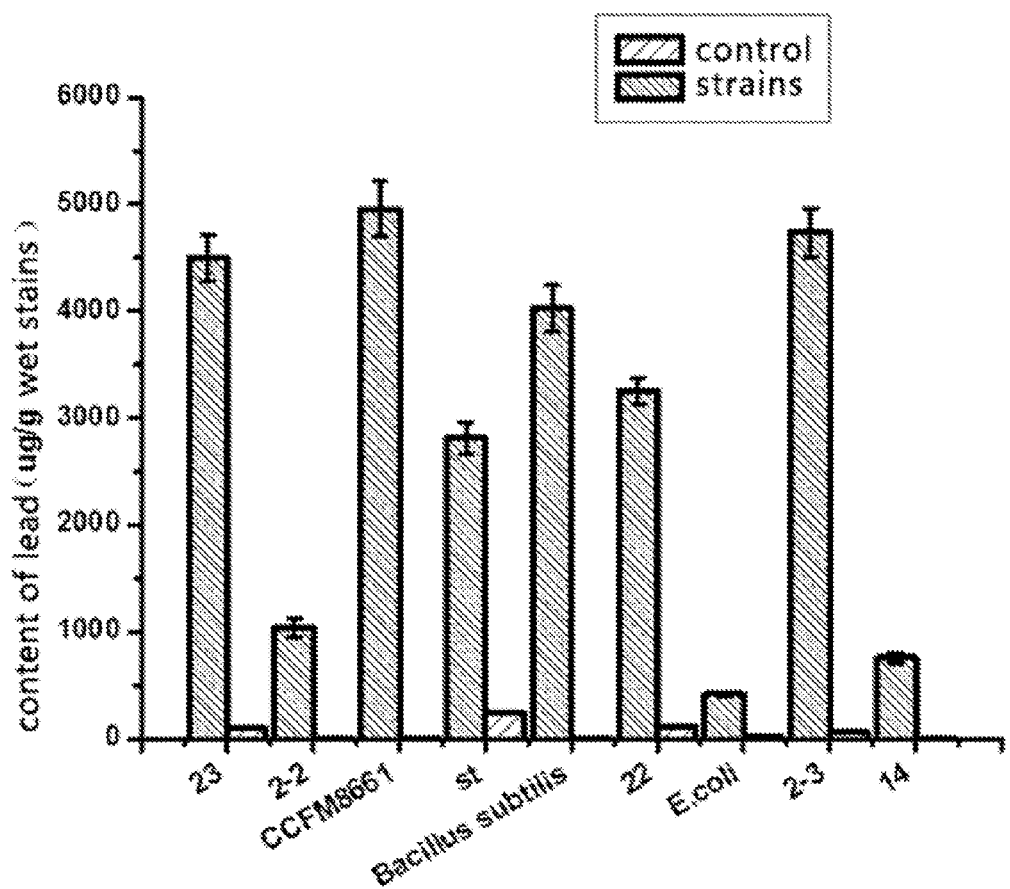
FIG. 2 shows the lead ions-binding abilities of lactobacilli, *Bacillus subtilis* and *Escherichia coli*.

The results are shown in FIG. 2. As depicted in FIG. 2, different strains have quite different lead binding capacities. *Lactobacillus plantarum* CCFM8661 has the highest absorption levels (4955.1 μg/g), and *E. coli* has a poorer lead binding capacity (398 μg/g) when compared with *Lactobacillus plantarum* CCFM8661.

Example 3

Tolerance dose experiment of mice fed with *Lactobacillus plantarum* CCFM8661

The frozen dry powder of *Lactobacillus plantarum* CCFM8661 is re-suspended in skim milk powder to obtain the suspension of $2.0 \times 10^9$ cfu/mL. 10 healthy Kunming male mice of 20 g are intragastrically administrated once a day. The death and weight statuses are observed for one week. These test results are shown in Table 1.

TABLE 1

Weight changes of mice fed with *Lactobacillus plantarum* CCFM8661 of $2.0 \times 10^9$ cfu/mL

| | Time (day) | | | | | | |
|---|---|---|---|---|---|---|---|
| | 1 | 2 | 3 | 4 | 5 | 6 | 7 |
| Weight (g) | 21.2 ± 1.5 | 21.9 ± 2.1 | 22.5 ± 2.2 | 23.5 ± 2.1 | 24.2 ± 1.9 | 24.9 ± 1.9 | 25.7 ± 1.8 |
| Death | — | — | — | — | — | — | — |

"—" means no death happened during the experimental period

The results in Table 1 show that 2.0×10$^9$ cfu/mL *Lactobacillus plantarum* CCFM8661 does not significantly affect these mice. They gain weight significantly without death and they have no significant pathological symptoms.

Example 4

Effect of *Lactobacillus plantarum* CCFM8661 on Reducing the Lead Level of Lead Exposed Mice 40 healthy male Kunming mice of 20-25 g are taken and randomly divided into four groups: namely negative control group, lead acetate model group, *Lactobacillus plantarum* CCFM8661 treatment group and calcium disodium edetate treatment group as positive control. The mice of negative control group are fed with ordinary drinking water and the mice of remaining three groups are fed with 1 g/L lead acetate solution to obtain the lead exposure models. The mice of *Lactobacillus plantarum* CCFM8661 treatment group are daily fed with the 2.0×10$^9$ cfu/mL skim milk suspension prepared in Example 3, and the mice of positive control treatment group are intraperitoneally injected with 5 g/L disodium edetate calcium agent every day. The blood is collected at the end of the experiment, and the liver, stomach and kidney are collected after these mice are sacrificed. These organs are processed in accordance with above digestion processes, and then the lead levels can be determined with above atomic absorption spectrophotometry of Example 2.

These test results are shown in FIG. 3. The lead levels of mice blood, liver, stomach and kidney in the *Lactobacillus plantarum* CCFM8661 group and calcium disodium edetate positive group are higher than that of the negative control group, but lower than that of the lead model control group. The lead levels of mice blood, liver, stomach and kidney in the *Lactobacillus plantarum* CCFM8661 group are significantly lower than that of the lead model control group (P<0.05), which shows that the intervention with the *Lactobacillus plantarum* CCFM8661 can virtually reduce the lead level of lead-exposed mice.

Example 5

Effect of *Lactobacillus plantarum* CCFM8661 on Alleviating Oxidative Damage Caused by Lead Exposure 40 healthy male Kunming mice of 20-25 g are taken and randomly divided into four groups: namely negative control group, lead acetate model group, *Lactobacillus plantarum* CCFM8661 treatment group and calcium disodium edetate (EDTANa$_2$Ca) treatment group as positive control. The mice of negative control group are fed with ordinary drinking water and the mice of remaining three groups are fed with 1 g/L lead acetate solution to obtain the lead exposure models. The mice of *Lactobacillus plantarum* CCFM8661 treatment group are daily fed with the 2.0×10$^9$ cfu/mL skim milk suspension prepared in Example 3 of this Specification, and the mice of positive control treatment group are intraperitoneally injected with 5 g/L disodium edetate calcium agent every day. The blood is taken at the end of the experiment, and the livers are taken out after these mice are sacrificed. These organs are processed with the Ellmam method (Ellmam, G. C. Tissue sulfhydryl groups. Archives of biochemistry and biophysics 82(1): 70-77.) and the malondialdehyde (MDA) kit of Nanjing Jiancheng Bioengineering Institute to determine the glutathione (GSH) and MDA levels. Results of the tests are shown in table 2.

TABLE 2

Effect of *Lactobacillus plantarum* CCFM8661 of this invention on recovering oxidative damage caused by lead exposure

| Group (liver) | GSH (mg/g protein) | MDA (nmol/mg protein) |
| --- | --- | --- |
| Blank control | 2.69 ± 0.40 | 0.11 ± 0.04 |
| Only lead | 1.63 ± 0.75$^a$ | 0.18 ± 0.03$^a$ |
| Lead + CCFM8661 | 2.46 ± 0.71$^b$ | 0.16 ± 0.04$^b$ |
| Lead + EDTANa$_2$Ca | 2.15 ± 0.50$^c$ | 0.15 ± 0.03$^c$ |

Note:
$^a$compared with the blank control group, P < 0.05;
$^b$compared with the lead model group P < 0.05;
$^c$compared with lead model group P < 0.05

In table 2, the liver GSH level in the group intervened with the *Lactobacillus plantarum* CCFM8661 of this invention is higher than that of the lead model group, but lower than that of the blank control group; the MDA level of the *Lactobacillus plantarum* CCFM8661 group is lower than that of the lead model control group, but higher than that of the blank control group. Compared with the lead model group, the GSH and MDA levels of the *Lactobacillus plantarum* CCFM8661 treatment group have significant difference (P<0.05). Glutathione (GSH) is an important in-vivo antioxidant, and malondialdehyde (MDA), an in-vivo marker for oxidative stress damage, is an end product of peroxidation that free radicals react with lipid in living organisms. As shown in Table 2, compared with the blank control group, the GSH level significantly decreases, and the MDA level significantly increases in the lead model group, which fully indicates that the lead exposure does cause the oxidative stress of mice. Compared with the lead model group, the GSH level significantly increases, and the MDA level significantly decreases in the *Lactobacillus plantarum* CCFM8661 group, which fully indicates that the *Lactobacillus plantarum* CCFM8661 can reduce the oxidative damage resulted from lead toxicity.

These animal experiments show that *Lactobacillus plantarum* CCFM8661 of this invention can significantly reduce the lead levels of blood and organs of lead-exposed mice, which improves the antioxidant indices of these mice, thus effectively alleviating lead toxicity.

Embodiment 1

Preparation of Cow Milk Containing the *Lactobacillus plantarum* CCFM8661

The raw skim milk is sterilized at 95° C. for 20 min, then cooled to 4° C., then added with the *Lactobacillus plantarum* CCFM8661 starter culture of this invention described in the Specifications with the concentration over 10$^6$ CFU/ml, and stored blow 4° C. to obtain the cow milk containing the *Lactobacillus plantarum* CCFM8661.

Embodiment 2

Preparation of Soybean Milk Containing the *Lactobacillus plantarum* CCFM8661

Soybeans are soaked in soft water at 80° C. for 2 h, peeled, ground with boiling water after removing the soaking water, and kept at 80° C. for 12 min. The ground soybeans are filtered using a 150 mesh sieve and centrifuged to obtain the centrifuge, i.e. crude soybean milk. It is heated to 140-150° C., and quickly added to a vacuum-cooling chamber for vacuuming. The off-flavour substances can be removed with water vapor. The crude soybean milk is cooled down to about 37° C.

after vacuuming degassing, and inoculated with the *Lactobacillus plantarum* CCFM8661 starter culture of this invention with the concentration over $10^6$ CFU/ml, and stored blow 4° C. to obtain the soybean milk containing the *Lactobacillus plantarum* CCFM8661.

Embodiment 3

Preparation of Fruit and Vegetable Juice Beverage Containing the *Lactobacillus plantarum* CCFM8661

The fresh fruits and vegetables are cleaned, juiced, sterilized in High Temperature Short Time (HTST) at 140° C. for 2 s, cooled to 37° C., then inoculated with the *Lactobacillus plantarum* CCFM8661 starter culture of this invention with the concentration over $10^6$ CFU/ml, and stored blow 4° C. to obtain the fruit and vegetable juice beverage containing the *Lactobacillus plantarum* CCFM8661

Embodiment 4

Preparation of Capsules Containing the *Lactobacillus plantarum* CCFM8661

The *Lactobacillus plantarum* CCFM8661 of this invention is cultured in MRS medium for 24 h, centrifuged at 4° C. and 4000 r/min for 20 min, washed with pH7.2 phosphate buffer twice, and re-suspended with sterilized skim milk to realize the final cell concentration of $1\times10^{10}$-$3\times10^{10}$ cfu/mL. The bacterial suspension is added to 3% by weight sodium alginate solution and sufficiently stirred so that cells are uniformly dispersed in the sodium alginate solution. The mixture is extruded to 2% by weight calcium chloride solution to obtain colloidal particles, and is standing for 30 min to achieve solidification. The particles are filtered, collected and freeze-dried for 48 h to obtain the powder containing *Lactobacillus plantarum* CCFM8661. The powder is put into pharmaceutical capsules sold on the market to obtain said capsules.

Embodiment 5

Preparation of Dairy, Soy, Fruit and Vegetable Products with the *Lactobacillus plantarum* CCFM8661

The *Lactobacillus plantarum* CCFM8661 by 3% weight of culture medium is inoculated in the culture medium sterilized at 115° C. for 10 min. The culture medium by total weight is made from 10% hydrolyzed skim milk, 0.5% glucose, 1.5% tryptone, 0.3% yeast extract, and water with the pH value of 6.8. Then the *Lactobacillus plantarum* CCFM8661 medium is inoculated at 37° C. for 18 h, washed twice with pH7.2 phosphate buffer, and re-suspended with protective agent to obtain the $10^{10}$ CFU/ml medium. The protective agent contains 100 g/L skimmed milk, 30 mL/L glycerol, 100 g/L maltodextrin, 150 g/L trehalose and 10 g/L sodium L-glutamate.

The suspension is pre-cultured at 37° C. for 60 min, and then freeze-dried to obtain the starter culture for dairy, soy, fruit and vegetable products Embodiment 6

Preparation of Fermented Milk Containing the *Lactobacillus plantarum* CCFM8661

Fresh milk is added with sugar, homogenized at 65° C. under 20 MPa, and sterilized at 95° C. for 5 min, cooled to 35° C., added with the mixed bacteria including the *Lactobacillus plantarum* CCFM8661 starter culture, commercial dry powder *Lactobacillus bulgaricus* starter culture and commercial dry powder *Streptococcus thermophilus* starter culture. The mass ratio is 1:1:1 and the inoculated bacterial is 0.03% of milk by weight. It is mixed evenly, fermented at 35° C., coagulated, and stored at 4° C. for 24 h to obtain the fermented milk.

Embodiment 7

Preparation of Tablets Containing the *Lactobacillus plantarum* CCFM8661

25.7 weight parts of the *Lactobacillus plantarum* CCFM8661 powder of this invention prepared by the freeze-drying method is evenly mixed with 55.0 weight parts of starch, 4.5 weight parts of cellulose derivatives, 12.0 weight parts of sodium carboxymethyl starch, 0.8 weight part of talc, 1.0 weight part of sucrose and 1.0 weight part of water, and processed to obtain wet particles by conventional method, then tablet pressed with a tablet machine, for example a machine produced and sold by South Pharmaceutical Machinery Factory, dried with a miniature drug dryer, for example a dryer produced and sold by Qingzhou Yikang Traditional Chinese Medicine Machinery Co., Ltd., and packed to obtain the tablets of this invention.

Embodiment 8

Preparation of Pills Containing the *Lactobacillus plantarum* CCFM8661

32.2 weight parts of the *Lactobacillus plantarum* CCFM8661 powder of this invention prepared by the freeze-drying method is evenly mixed with 48.0 weight parts of microcrystalline cellulose, 4.5 weight parts of polyvinyl pyrrolidone, 10.0 weight parts of calcium carbonate, 2.8 weight parts of magnesium stearate, 1.3 weight parts lecithin of and 1.2 weight parts of ethanol, and then conventional amount of refining honey are added to obtain the pills of this invention.

The invention claimed is:

1. A method for preparing fermented food comprising: a) providing a fermentation medium that is prepared by mixing water, milk, glucose, tryptone and yeast extract, adjusting pH to neutral, and sterilizing; b) providing a protective agent by mixing skim milk powder, glycerol, malt dextrin, trehalose, L-sodium glutamate and water; c) inoculating said fermentation medium with *Lactobacillus plantarum* CCFM8661 deposited at the General Microbiology Culture Collection Center of China Committee for Culture Collection of Microorganisms under accession number CGMCC No. 5494, culturing at 37° C. for 12-24 h, washing 2-4 times with phosphate buffer and re-suspending with said protective agent which yields the medium with the concentration of the *Lactobacillus plantarum* CCFM8661 at the range from $10^9$ to $10^{10}$ CFU/ml; d) culturing at 37° C., and then freeze-drying which yields a starter culture; e) mixing the starter culture with an edible composition at the concentration of the *Lactobacillus plantarum* CCFM8661 above $10^6$ CFU/ml.

2. The fermented food according to claim 1, wherein the edible composition is selected from the group consisting of a dairy product, a soy product, a fruit and vegetable product.

3. The fermented food according to claim 2, wherein the dairy product is selected from the group consisting of milk, sour cream and cheese; the soybean product is selected from the group consisting of soybean milk, fermented soybean and soybean paste; and the fruit and vegetable product is selected from the group consisting of cucumber, carrot, beet, celery and cabbage.

* * * * *